(12) United States Patent
Choi et al.

(10) Patent No.: US 7,306,944 B2
(45) Date of Patent: Dec. 11, 2007

(54) ADVANCED CELL-TRANSDUCING TRANSPORT DOMAIN-TARGET PROTEIN-TRANSPORT DOMAIN FUSION PROTEIN AND USES THEREOF

(75) Inventors: Su-Young Choi, Chuncheon-si (KR); Jin-Seo Park, Chuncheon-si (KR); Kyu-Hyung Han, Chuncheon-si (KR); Jin-Hee Choi, Chuncheon-si (KR)

(73) Assignee: Polymer Ventures, Inc., Charleston, SC (US)

( * ) Notice: Subject to any disclaimer, the term of this patent is extended or adjusted under 35 U.S.C. 154(b) by 286 days.

(21) Appl. No.: 10/488,743

(22) PCT Filed: Mar. 13, 2003

(86) PCT No.: PCT/KR03/00490

§ 371 (c)(1),
(2), (4) Date: Aug. 23, 2004

(87) PCT Pub. No.: WO2004/039846

PCT Pub. Date: May 13, 2004

(65) Prior Publication Data

US 2006/0165634 A1    Jul. 27, 2006

(30) Foreign Application Priority Data

Oct. 31, 2002   (KR) ............... 10-2002-0066981

(51) Int. Cl.
*A61K 8/02* (2006.01)
*A61K 8/64* (2006.01)
*C12N 9/02* (2006.01)
*C12N 9/99* (2006.01)
*C12P 21/04* (2006.01)

(52) U.S. Cl. ............. 435/401; 435/189; 435/184; 435/69.7; 424/94.4; 424/400

(58) Field of Classification Search ......... 435/69.7, 435/184, 189
See application file for complete search history.

(56) References Cited

U.S. PATENT DOCUMENTS

2004/0043463 A1* 3/2004 Rao ................. 435/184
2006/0141598 A1* 6/2006 Terlecky et al. ...... 435/189

OTHER PUBLICATIONS

Park et al. (Molecul. Cells . (2002) 13 , pp. 202-208).*

* cited by examiner

*Primary Examiner*—Rebecca E. Prouty
*Assistant Examiner*—Md. Y. Meah
(74) *Attorney, Agent, or Firm*—Nelson Mullins Riley & Scarborough, LLP

(57) ABSTRACT

The present invention provides a fusion protein which delivers a functional protein or peptide into a cell at enhanced efficiency. The fusion protein of the present invention is a transduction domain-target protein-transduction domain fusion protein, wherein the transduction domain, which comprises 6-12 amino acid residues whose more than ¾ consist of arginine or lysine residues, is covalently bonded to each of the amino- and carboxyl-terminal ends of the target protein. Green fluorescence protein and Cu/Zn-superoxide dismutate (SOD) are used as the target protein.

4 Claims, 11 Drawing Sheets

A

B

SEQUENCE LISTING

<160> NUMBER OF SEQ ID NOS: 10

<210> SEQ ID NO 1
<211> LENGTH: 27
<212> TYPE: DNA
<213> ORGANISM: Aequorea victoria

<400> SEQUENCE: 1
ctcgaggtga gcaagggcga ggagctg                27

<210> SEQ ID NO 2
<211> LENGTH: 33
<212> TYPE: DNA
<213> ORGANISM: Aequorea victoria

<400> SEQUENCE: 2
ggatccttac ttgtacagct cgtccatgcc gag          33

<210> SEQ ID NO 3
<211> LENGTH: 29
<212> TYPE: DNA
<213> ORGANISM: Human immunodeficiency virus type 1

<400> SEQUENCE: 3
taggaagaag cggagacagc gacgaagac               29

<210> SEQ ID NO 4
<211> LENGTH: 31
<212> TYPE: DNA
<213> ORGANISM: Human immunodeficiency virus type 1

<400> SEQUENCE: 4
tcgagtcttc gtcgctgtct ccgcttcttc c                           31

<210> SEQ ID NO 5
<211> LENGTH: 27
<212> TYPE: DNA
<213> ORGANISM: Homo sapiens

<400> SEQUENCE: 5
ctcgaggcga cgaaggccgt gtgcgtg                                27

<210> SEQ ID NO 6
<211> LENGTH: 27
<212> TYPE: DNA
<213> ORGANISM: Homo sapiens

<400> SEQUENCE: 6
ggatccttat tgggcgatcc caattac                                27

<210> SEQ ID NO 7
<211> LENGTH: 768
<212> TYPE: DNA
<213> ORGANISM: Artificial
<220> FEATURE:
<223> OTHER INFORMATION: recombinant polynucleotide coding HIV-1 Tat-
      green fluorescence protein-Tat fusion protein

<400> SEQUENCE: 7
aggaagaagc ggagacagcg acgaagagtg agcaagggcg aggagctgtt caccggggtg     60
gtgcccatcc tggtcgagct ggacggcgac gtaaacggcc acaagttcag cgtgtccggc    120
gagggcgagg gcgatgccac ctacggcaag ctgaccctga agttcatctg caccaccggc    180
aagctgcccg tgccctggcc caccctcgtg accaccctga cctacggcgt gcagtgcttc    240
agccgctacc ccgaccacat gaagcagcac gacttcttca agtccgccat gcccgaaggc    300
tacgtccagg agcgcaccat cttcttcaag gacgacggca actacaagac cgcgccgag     360 gtgaagttcg agggcgacac cctggtgaac cgcatcgagc tgaagggcat cgacttcaag    420
gaggacggca acatcctggg gcacaagctg gagtacaact acaacagcca caacgtctat    480
atcatggccg acaagcagaa gaacggcatc aaggtgaact tcaagatccg ccacaacatc    540
gaggacggca gcgtgcagct cgccgaccac taccagcaga acaccccat cggcgacggc     600 cccgtgctgc tgcccgacaa ccactacctg agcacccagt ccgccctgag caaagacccc    660
aacgagaagc gcgatcacat ggtcctgctg gagttcgtga ccgccgccgg gatcactctc    720
ggcatggacg agctgtacaa gaggaagaag cggagacagc gacgaaga              768

<210> SEQ ID NO 8
<211> LENGTH: 256
<212> TYPE: PRT
<213> ORGANISM: artificial
<220> FEATURE:
<223> OTHER INFORMATION: Amino acid sequence of tat-GFP-tat fusion
      protein

<400> SEQUENCE: 8

Arg Lys Lys Arg Arg Gln Arg Arg Arg Val Ser Lys Gly Glu Glu Leu

```
             1               5                  10                15
          Phe Thr Gly Val Val Pro Ile Leu Val Glu Leu Asp Gly Asp Val Asn
                          20                  25                  30
          Gly His Lys Phe Ser Val Ser Gly Glu Gly Glu Gly Asp Ala Thr Tyr
                      35                  40                  45
          Gly Lys Leu Thr Leu Lys Phe Ile Cys Thr Thr Gly Lys Leu Pro Val
                  50                  55                  60
          Pro Trp Pro Thr Leu Val Thr Thr Leu Thr Tyr Gly Val Gln Cys Phe
          65                  70                  75                  80
          Ser Arg Tyr Pro Asp His Met Lys Gln His Asp Phe Phe Lys Ser Ala
                              85                  90                  95
          Met Pro Glu Gly Tyr Val Gln Glu Arg Thr Ile Phe Phe Lys Asp Asp
                          100                 105                 110
          Gly Asn Tyr Lys Thr Arg Ala Glu Val Lys Phe Glu Gly Asp Thr Leu
                      115                 120                 125
          Val Asn Arg Ile Glu Leu Lys Gly Ile Asp Phe Lys Glu Asp Gly Asn
                  130                 135                 140
          Ile Leu Gly His Lys Leu Glu Tyr Asn Tyr Asn Ser His Asn Val Tyr
          145                 150                 155                 160
          Ile Met Ala Asp Lys Gln Lys Asn Gly Ile Lys Val Asn Phe Lys Ile
                              165                 170                 175
          Arg His Asn Ile Glu Asp Gly Ser Val Gln Leu Ala Asp His Tyr Gln
                          180                 185                 190
          Gln Asn Thr Pro Ile Gly Asp Gly Pro Val Leu Leu Pro Asp Asn His
                      195                 200                 205
          Tyr Leu Ser Thr Gln Ser Ala Leu Ser Lys Asp Pro Asn Glu Lys Arg
                  210                 215                 220
          Asp His Met Val Leu Leu Glu Phe Val Thr Ala Ala Gly Ile Thr Leu
          225                 230                 235                 240
          Gly Met Asp Glu Leu Tyr Lys Arg Lys Lys Arg Arg Gln Arg Arg Arg
                              245                 250                 255

<210> SEQ ID NO 9
<211> LENGTH: 530
<212> TYPE: DNA
<213> ORGANISM: Artificial
<220> FEATURE:
<223> OTHER INFORMATION: Recombinant polynucleotide coding HIM-1 Tat-
      Human superoxide dismutase-Tat fusion protein

<400> SEQUENCE: 9
taggaagaag cggagacagc gacgaagact cgaggcgacg aaggccgtgt gcgtgctgaa       60
gggcgacggc ccagtgcagg gcatcatcaa tttcgagcag aaggaaagta atggaccagt      120
gaaggtgtgg ggaagcatta aaggactgac tgaaggcctg catggattcc atgttcatga      180
gtttggagat aatacggcag gctgtaccag tgcaggtcct cactttaatc ctctatccag      240
aaaacacggt gggccaaagg atgaagagag catgttggaa gacttgggca atgtgactgc      300
tgacaaagat ggtgtggccg atgtgtctat tgaagattct gtgatctcac tctcaggaga      360
ccattgcatc attggccgca cactggtggt ccatgaaaaa gcagatgact gggcaaagg       420 tggaaatgaa gaaagtacaa agacaggaaa cgctggaagt cgtttggctt gtggtgtaat      480
tgggatcgcc aataaggat cctaggaaga agcggagaca gcgacgaaga               530

<210> SEQ ID NO 10
<211> LENGTH: 172
```

```
<212> TYPE: PRT
<213> ORGANISM: artificial
<220> FEATURE:
<223> OTHER INFORMATION: Recombinant polypeptide sequence of HIM-1 Tat-
      Human superoxide dismutase-Tat fusion protein

<400> SEQUENCE: 10

Arg Lys Lys Arg Arg Gln Arg Arg Met Ala Thr Lys Ala Val Cys
1               5                   10                  15

Val Leu Lys Gly Asp Gly Pro Val Gln Gly Ile Ile Asn Phe Glu Gln
            20                  25                  30

Lys Glu Ser Asn Gly Pro Val Lys Val Trp Gly Ser Ile Lys Gly Leu
            35                  40                  45

Thr Glu Gly Leu His Gly Phe His Val His Glu Phe Gly Asp Asn Thr
            50                  55                  60

Ala Gly Cys Thr Ser Ala Gly Pro His Phe Asn Pro Leu Ser Arg Lys
65                  70                  75                  80

His Gly Gly Pro Lys Asp Glu Glu Arg His Val Gly Asp Leu Gly Asn
                85                  90                  95

Val Thr Ala Asp Lys Asp Gly Val Ala Asp Val Ser Ile Glu Asp Ser
            100                 105                 110

Val Ile Ser Leu Ser Gly Asp His Cys Ile Ile Gly Arg Thr Leu Val
            115                 120                 125

Val His Glu Lys Ala Asp Asp Leu Gly Lys Gly Gly Asn Glu Glu Ser
    130                 135                 140

Thr Lys Thr Gly Asn Ala Gly Ser Arg Leu Ala Cys Gly Val Ile Gly
145                 150                 155                 160

Ile Ala Gln Arg Lys Lys Arg Arg Gln Arg Arg Arg
                165                 170
```

ADVANCED CELL-TRANSDUCING TRANSPORT DOMAIN-TARGET PROTEIN-TRANSPORT DOMAIN FUSION PROTEIN AND USES THEREOF

TECHNICAL FIELD

The present invention relates to a fusion protein of delivering a functional protein or peptide into a cell at increased efficiency, and uses thereof.

BACKGROUND ART

Recently, as the fact that various diseases are caused by the abnormal activity of cell proteins is known, the development of drugs capable of adjusting the activity of such proteins to treat fatal human diseases becomes the object of interest in the whole world.

In a description of the present invention, superoxide dismutase related to reactive oxygen species is mentioned as one example of the cell proteins. However, it is to be understood that the scope of the target proteins in the present invention is not limited only to this protein.

Reactive oxygen species are inevitably produced as byproducts of intracellular metabolism in all living beings where energy is obtained using oxygen. Such reactive oxygen species cause damage to biopolymers, such as intracellular protein, nucleic acid and fat, and have a deep connection with the progression of various diseases of the human body. Particularly, they are involved in carcinogenesis processes, apoplexy, arthritis, radiation damage and inflammatory reaction, and act as an important factor of promoting aging even in a normal aging process [Floyd, R. A., FASEB J. 4, 2587-2597 (1990); Anderson, W. F., Human gene therapy, Nature 392, 25-30 (1998); and Halliwell B. and Gutteridge J. M. C., Free radicals in biology and medicine, Oxford University Press, Oxford (1999)].

Diseases related to Cu/Zn-superoxide dismutase are summarized in Table 1 below.

TABLE 1

| Categories | Concrete examples |
|---|---|
| Inflammatory/immune damage | Glomerulonephritis, vasculitis, autoimmune diseases and the like |
| Ischemia | Stroke, myocardial infarction, arrhythmia, angina pectoris and the like |
| Drug and toxic substance-inducing reaction | — |
| Iron overload (tissue and serum) | Idiopathic hemochromotosis and the like |
| Radiation-related damage | Nuclear bombing, radiation therapy and the like |
| Aging | Progeria, and disease-related aging |
| Red blood cells | Sickle-cell anemia, malaria and the like |
| Bronchi | A result of smoking, emphysema and the like |
| Heart and cardiovascular systems | Cardiomyopathy |
| Kidneys | Autoimmune nephrotic syndrome |
| Stomach and intestines | Betelnut-related oral cancer |
| Abnormal conditions of brains/nervous system/nervous muscles | Hypoxia, Alzheimer's disease, Parkinson's disease and the like |
| Eye | Cateract and the like |
| Skin | Diseases caused by UV irradiation, and the like |

*Quoted from "Free radicals in biology and medicine", Oxford University Press, Oxford, pp 618-619.

Known reactive oxygen species include $_1O_2$, OH, $O_2$, $H_2O_2$ and the like. They are produced by various enzymatic reactions, and play an important role in the biosynthesis and immune function of various physiologically active substances, and drug metabolism. However, if they are overproduced by external radiation, UV, environmental pollution and various stresses, they can rather cause damage to the living body. For this reason, the living body has enzymes, such as SOD, catalase and peroxidase, for their defensive function, and if its aging is started, the balance of the skin will be upset and the ability of this enzyme to protect the skin from various reactive oxygen species will be reduced.

Thus, a need to protect the skin from such reactive oxygen species is being increased, and SOD, lactoferrin, and antioxidants, etc., are used or developed as raw materials of cosmetics for the removal of the reactive oxygen species. However, SOD was not advantageously employed in a cosmetic composition in spite of its ability to remove the reactive oxygen species, because it has the nature of enzymatic protein and thus problems in that it is difficultly soluble in lipid, has insufficient stability, and is impermeable to the skin's keratin layer due to its molecular weight of more than 30,000 Daltons.

Cu/Zn-superoxide dismutase is an important intracellular defensive enzyme of preventing the cellular damage caused by free radical toxicity and oxygen-radical damage [Fridovich, I., Annu. Rev. Biochem., 64, 97-112 (1995)]. Since all polymers in the living body are always exposed to this harmful action of the oxygen radical, an interest to use the Cu/Zn-superoxide dismutase for the treatment of various diseases is being increased.

Recently, there are many attempted methods for clinically applying the Cu/Zn-superoxide dismutase. Methods for delivering the Cu/Zn-superoxide dismutase into the living body, which have been developed till now, can be broadly classified into the following three categories. First, there is a method of conjugating polyethylene glycol, ficoll, lecithin, albumin and the like to the Cu/Zn-superoxide dismutase [Del Zoppo, G. J. et al., Drugs 54, 9-38, (1997); and Muzykantov, V. R. et al., Proc. Natl. Acad. Sci. USA 93, 5213-5218, (1996)]. Second, there is a method of encapsulating the Cu/Zn superoxide dismutase with liposome [Perdereau, B. et al., Bull. Cancer 81, 659-669 (1994)]. Third, there is a genetic therapy where the Cu/Zn superoxide dismutase gene is transduced into cells to induce the overexpression of the enzyme in the cells [Okumura, K. et al., Pharm. Res. 14, 1223-1227; (1997); Lehmann, T. G. et al., Transplantation 69, 1051-1057 (2000); and Liu, R. et al., Hum. Gene Ther. 8, 585-595 (1997)].

Among such methods, the genetic therapy is most attracted, and many studies to use the Cu/Zn-superoxide dismutase gene for the treatment of diseases have been conducted. However, the genetic therapy has various problems in that a method of delivering the gene into a cell is not easy, the percent expression of the gene in a target cell is low, and it is very difficult to artificially adjust the amount of expression of the protein in the target cell [Verma, I. M. et al., Nature 389, 239-242 (1997)].

As another method of delivering a therapeutic drug or protein into a cell, a method of directly delivering a target protein through a cell membrane to a cell can be contemplated. However, the therapeutic drug or protein is very difficult to pass through the cell membrane due to its size or various biochemical properties. It is generally known that substances with a molecular weight above 600 are almost impossible to pass through the cell membrane.

It was recently found that a Tat (transactivator of transcription) protein as a kind of human immunodeficiency virus type-1 proteins is efficiently passed through the cell membrane such that it is easily delivered into a cytoplasm.

This function appears due to the property of a protein transduction domain as the middle domain of the Tat protein, and its precise mechanism is yet unknown [Frankel, A. D. and Pabo, C. O., Cell 55, 1189-1193 (1988); Green, M. and Loewenstein, P. M., Cell 55, 1179-1188 (1988); Ma, M. and Nath, A., J. Virol. 71, 2495-2499 (1997); and Vives, E., Brodin, P. and Lebleu, B., J. Biol. Chem. 272, 16010-16017 (1997)]. However, it seems that a certain receptor or carrier is not involved in the passage of the Tat protein through the cell membrane, and this passage of the Tat protein is caused by the direct interaction between the protein transduction domain of the Tat protein and the lipid double layer of the cell membrane [Vives, E. et al., J. Biol. Chem. 272, 16010-16017 (1997); and Derossi, D. et al., J. Biol. Chem. 271, 18188-18193 (1996)].

Recent studies showed that when heteroproteins, such as ovalbumin, β-galactosidase, and horseradish peroxidase, was administered in a form fused with an HIV-1 Tat protein, they were delivered directly into each tissue of the living body and a cultured cell [Fawell, S. et al., Proc. Natl. Acad. Sci. USA 91, 664-668 (1994); Schwartze, S. R. et al., Science. 285, 1569-1572 (1999); and Watson, K. and Edward, R. J., Biochem. Pharmacol., 58, 1521-1528 (1999)]. This test result suggests that the Tat protein has the ability to deliver itself and also other macromolecules into the cell.

However, it is not that substantially all proteins are delivered by the Tat protein. Furthermore, whether all the proteins delivered by the Tat protein into the cell show biological activity is not yet certainly established.

Moreover, the present inventors conducted an intracellular transduction test for the following fusion proteins: a fusion protein where a HIV Tat protein transduction domain (residues 49-57) is covalently bonded to the amino-terminal end, a fusion protein where an oligolysine transduction domain having 6-12 lysines are covalently bonded to the amino-terminal end; and a fusion protein where a basic transduction domain from which 2 or 3 residues of HIV Tat residues 48-57 had been deleted, are covalently bound to the amino-terminal end. The test results showed that the fusion proteins had the ability to be smoothly transduced into the cell (Korean patent laid-open publication Nos. 2002-10446 and 2002-67108).

DISCLOSURE OF INVENTION

Therefore, an object of the present invention is to deliver or express a target protein in a cell at high efficiency without encountering the problems of the prior art, such that the target protein has activity in the cell.

Another object of the present invention is to deliver or express a superoxide dismutase in a cell at high efficiency without encountering the problems of the prior art, such that the superoxide dismutase has activity in the cell.

Still another object of the present invention is to provide cosmetics which comprises a transduction domain-superoxide dismutase fusion protein, so that they are delivered into the epidermal, dermal and subcutaneous fat layers of the skin by virtue of the fusion protein and thus have the excellent ability to remove reactive oxygen species.

To achieve the above objects, the present inventors fused a transduction domain to a human Cu/Zn-superoxide dismutase, and in a test using a HeLa cell, we have examined if the fusion protein is effectively transduced into a cell. Furthermore, the present inventors developed a method of mass-producing and purifying a transduction domain-superoxide dismutase-transduction domain fusion protein.

In order to more efficiently deliver a functional protein or peptide into a cell and to make the functional protein shows increased activity in the cell, the present invention provides a transduction domain-functional protein fusion protein, and pharmaceutical and cosmetic compositions using this fusion protein.

The transduction domain-target protein-transduction domain fusion protein of the present invention can be produced according to a general chemical bonding method in addition to a genetic recombinant method.

The present invention provides a transduction domain-target protein-transduction domain fusion protein having the ability to be transduced into a cell, wherein the transduction domain, which comprises 6-12 amino acid residues whose more than ¾ consist of arginine or lysine residues, is covalently bonded to each of the amino- and carboxyl-terminal ends of the target protein. The transduction domains located at both terminal ends of the target protein do not need to consist of the same residue.

In the transduction domain-target protein-transduction domain fusion protein of the present invention, the transduction domain preferably consists of 9 amino acid residues.

In the present invention, the transduction domain is preferably one or more selected from HIV tat residues 49-57, oligolysine, oligoarginine, and oligo(lysine/arginine).

Moreover, the target protein is preferably selected from the group consisting of a therapeutic molecule, a preventive molecule, and a diagnostic molecule.

Furthermore, the target protein is preferably a Cu/Zn-superoxide dismutase or functional equivalents thereof.

In another embodiment, the present invention provides a cosmetic composition which contains, as an active ingredient, the transduction domain-target protein-transduction domain fusion protein having the ability to be transduced into a cell.

In the cosmetic composition of the present invention, the target protein is preferably a Cu/Zn-superoxide dismutase or functional equivalents thereof.

Moreover, the cosmetic composition of the present invention is preferably in the form of toilet water, gel, water-soluble liquid, oil-in-water (O/W), or water-in-oil (W/O).

In yet another embodiment, the present invention provides a pharmaceutical composition which contains the transduction domain-target protein-transduction domain fusion protein as an active ingredient, and a pharmaceutically acceptable carrier.

In the pharmaceutical composition of the present invention, the target protein is preferably a Cu/Zn-superoxide dismutase or functional equivalents thereof.

The pharmaceutical composition containing the transduction domain-target protein-transduction domain fusion protein as an active ingredient can be formulated into an oral or injection form by a conventional method together with a pharmaceutically acceptable carrier. Examples of the oral composition include tablets and gelatin capsules, etc. In addition to the active ingredient, the oral composition may, if necessary, contain a diluent (e.g., lactose, dextrose, sucrose, mannitol, sorbitol, cellulose and/or glycine), and a lubricant (e.g., silica, talc, stearic acid, and magnesium and calcium salts thereof, and/or polyethylene glycol). The tablets preferably contain a binder (e.g., magnesium aluminum silicate, starch paste, gelatin, methyl cellulose, sodium carboxymethylcellulose, and/or polyvinylpyrrolidone), and if necessary, a disintegrant (e.g., starch, agar, alginic acid or a sodium salt thereof) or a boiling mixture and/or an absorbing agent, a coloring agent, a flavoring agent and a sweetening agent. The injection composition is preferably in the form of isotonic aqueous solution or suspension, and it is sterilized and if necessary, contains aids (preservatives, stabilizers, wetting agents, emulsifier, accelerators, salts for adjusting osmotic pressure, and/or buffers). In addition, they may also contain therapeutically useful substances.

The pharmaceutical formulation thus produced can be administered orally or by parenteral routes, including intravenous, subcutaneous, intra-abdominal or topical routes, at a dosage of 0.0001-2 mg/kg one to several times a day. The dosage for a certain patient can vary depending on the patient's body weight, age, sex and health, the period of time for administration, percent excretion, and the severity of diseases, etc.

Furthermore, the composition of the present invention can be formulated into cream, ointment, gel, lotion, and toilet water, etc., before use, and a form into which the composition is formulated before use can be easily determined by a person skilled in the art.

Moreover, each of the lotion, gel, essence, cream, toilet water and the like, which contain the transduction domain-target protein-transduction domain fusion protein of the present invention as an active ingredient, can be easily produced in any form according to a conventional method, and conveniently added to basic cosmetics before use.

For example, in producing cream, the fusion protein of the present invention is added to a general oil-in-water (O/W) or water-in-oil (W/O) cream base, to which perfumes, chelating agents, pigments, antioxidants, preservatives and the like are added in combination with synthetic or natural materials, such as proteins, minerals and vitamins, for the purpose of improving the physical properties of the cream.

As used herein, the term "target protein" means a therapeutic, preventive or diagnostic molecule, which forms a covalent bond with the HIV-1 Tat transduction domain and shows activity when delivered into a cell. In fact, this term is not limited only to a pure protein, but intended to include peptide, polypeptide, sugar protein bound to saccharides, peptidoglycan.

As used herein, the term "transduction domain" means a domain which forms a covalent bond with peptide, protein, oligopeptide, sugar protein bound to saccharides, peptidoglycan or polypeptide, and allows the organic compounds to be transduced into a cell without the need of a separate receptor or carrier, or energy. This transduction domain consists of 6-12 amino acid residues, more than ¾ of which consist of arginine or lysine residues. Typical examples of this transduction domain include HIV-1 Tat (amino acids 48-57), oligolysine, oligoarginine, oligo(lysine/arginine) and the like. A more preferred example of the inventive transduction domain is one consisting of 9 amino acid residues whose more than ¾ consist of arginine or lysine residues.

In the specification and claims, the term "delivering" protein, oligopeptide, sugar protein, oligopeptide, or polypeptide, etc, into a cell, was used exchangeably with the expressions "introducing", "infiltrating", "transporting", "transducing" and "passing".

Lane M: SDS Marker; lane GFP: GFP; Lane TG: Tat-GFP; lane GT: GFP-Tat; and Lane TGT: Tat-GFP-Tat.

FIG. 3a shows the results of Western blot analysis to examine the intracellular transduction of denatured Tat-GFP, GFP-Tat, and Tat-GFP-Tat fusion proteins. For the Western blot analysis, 1M of the fussion proteins were added to HeLa cells and then the cells were cultured for 1 hour.

FIG. 3b diagrammatically shows the intensity of line according to Western blot results for proteins introduced into cells.

Figure 4:
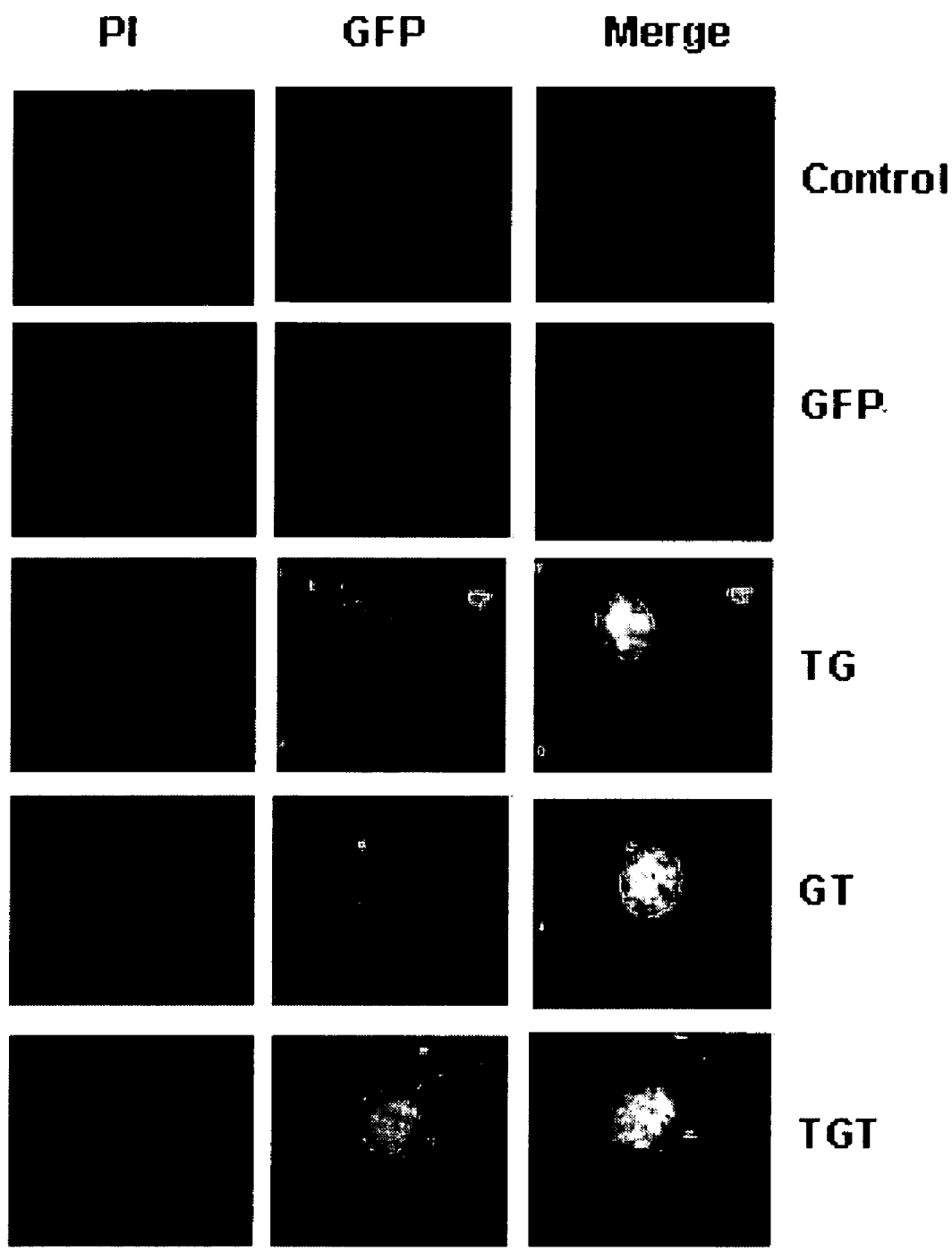

FIG. 4 shows the images of Tat-GFP, GFP-Tat, and Tat-GFP-Tat fusion proteins taken with a confocal fluorescent microscope, after the proteins were introduced into cells. Each section is as follows:

control: untreated cell; GFP: 1M control GFP; TG: 1M Tat-GFP 1M; GT: 1M GFP-Tat; and TGT: 1M Tat-GFP-Tat.

Figure 5:
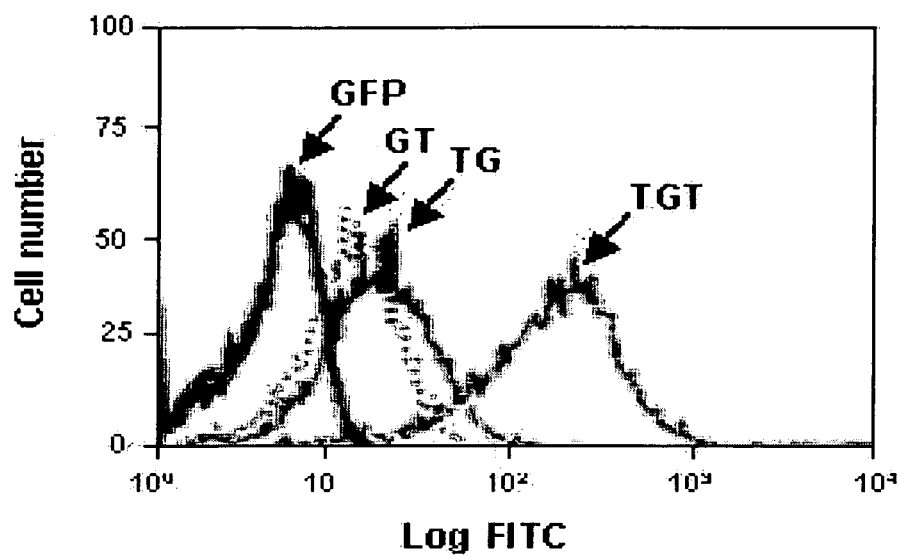

FIG. 5 shows the results of FACS analysis to examine the efficiency of intracellular transduction of GFP fusion proteins. For the FACS analysis, each of the fusion proteins was added to cells at a 2M concentration and then the cells were cultured for 30 minutes.

TG: Tat-GFP; GT: GFP-Tat; and TGT: Tat-GFP-Tat.

Figure 6:
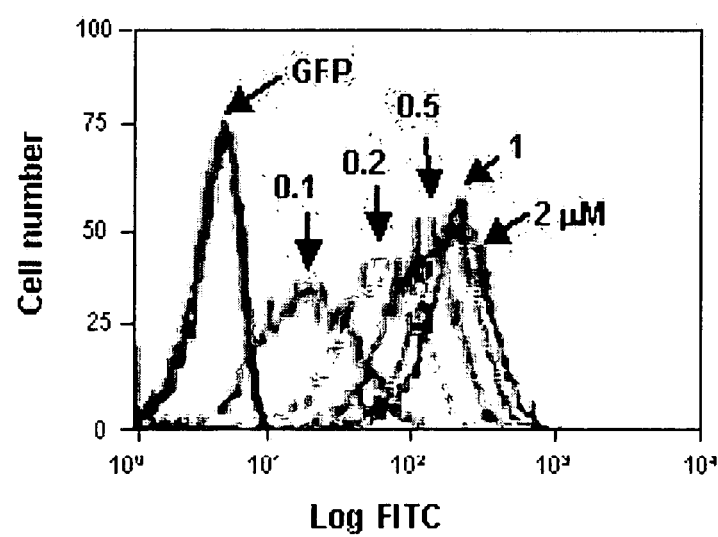

FIG. 6 shows the results of FACS analysis for cells, which were added with Tat-GFP-Tat fusion protein of various concentrations and cultured for 30 minutes. Control GFP was added to cells at the maximum concentration of 2M.

FIG. 7a shows the results of Western blot analysis to examine the efficiency of intracellular transduction of Tat-GFP-Tat fusion proteins which were purified in native and denatured states. For the Western blot analysis, each of the fusion proteins was added to cells at a 1M concentration and then the cells were cultured for 1 hour.

Lane con: an untreated cell; lane GFP: control GFP; lane "native": Tat-GFP-Tat purified in a native state; and lane "denatured": Tat-GFP-Tat purified in a denatured state.

FIG. 7b is a graphic diagram showing the intensity of lines according the results of FIG. 7a.

Figure 8:
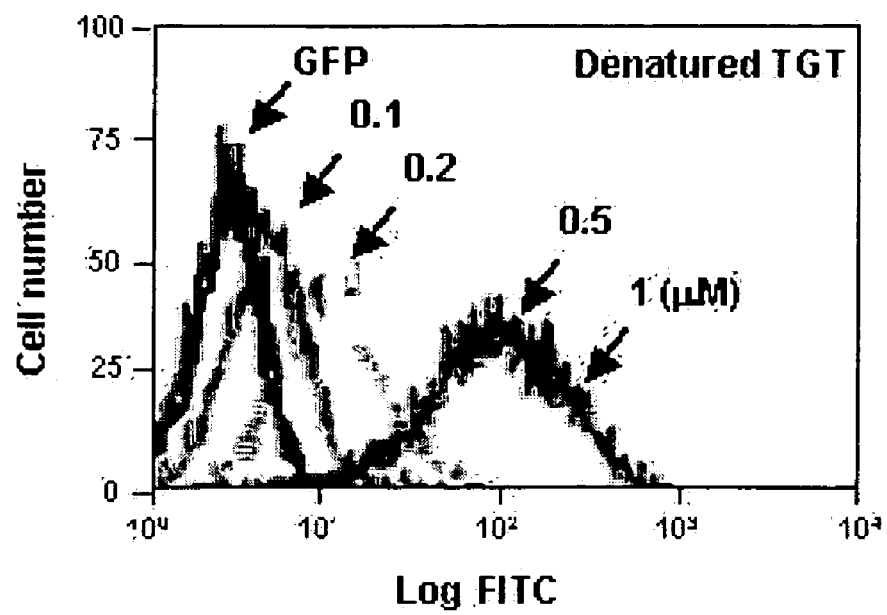
Figure 8:
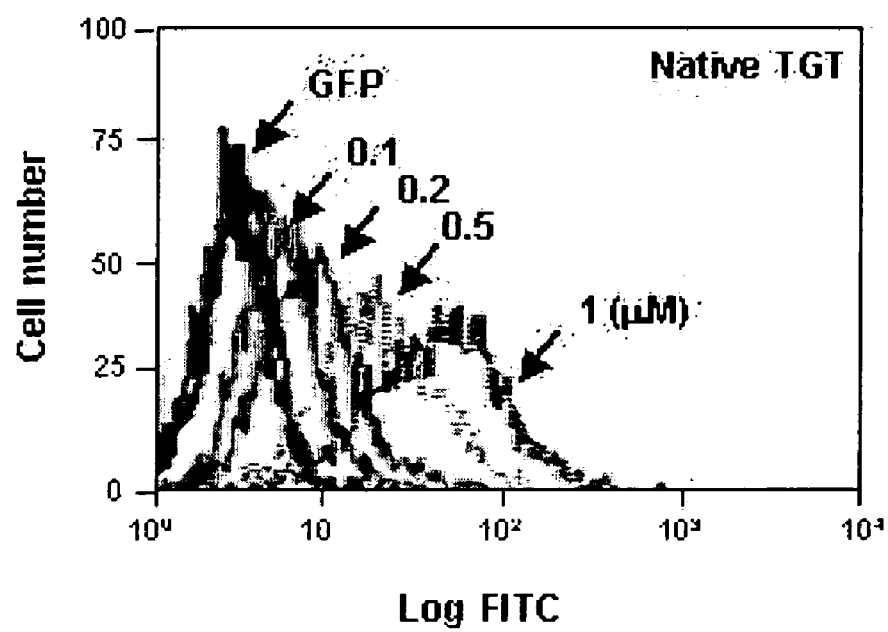

FIG. 8 shows the results of FACS analysis to examine the efficiency of intracellular transduction of Tat-GFP-Tat fusion proteins purified in native and denatured states. For the FACS analysis, the fusion proteins were added to cells at various concentrations and then the cells were cultured for 1 hour.

FIG. 8a shows the results of analysis for a Tat-GFP-Tat fusion protein, which was purified in a denatured state and added to cells at concentrations of 0.1M, 0.2M, 0.5M, and 1M.

FIG. 8b shows the results of analysis on a Tat-GFP-Tat fusion protein, which was purified in a native state and added to cells at concentrations of 0.1M, 0.2M, 0.5M, and 1M.

Figure 9:
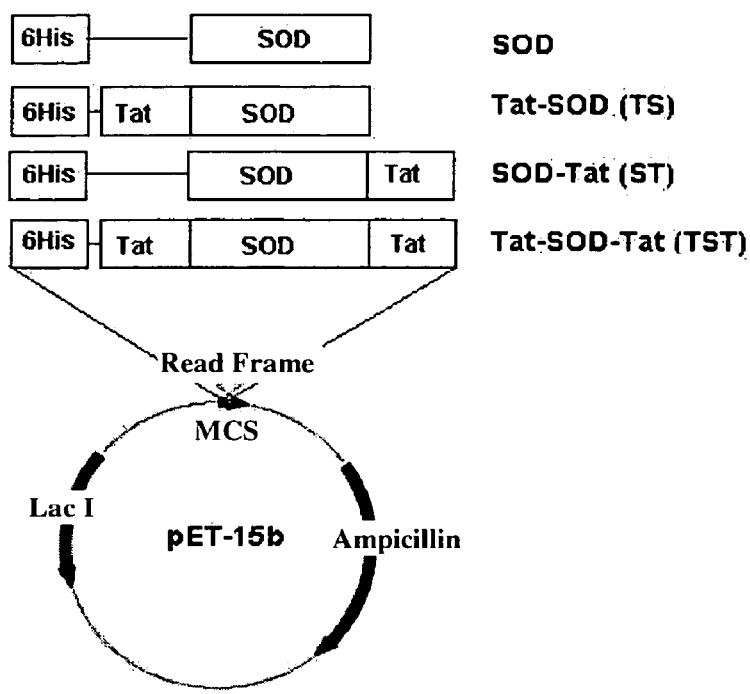

FIG. 9 is a schematic diagram of Tat-SOD, SOD-Tat, Tat-SOD-Tat, and SOD expression vectors. The vectors were produced by fusing a synthesized Tat protein to the amino- or carboxyl- terminal end or both terminal ends of SOD. pSOD as an SOD expression vector was produced by inserting the coding sequence of SOD into a pET-15b vector.

Figure 10:
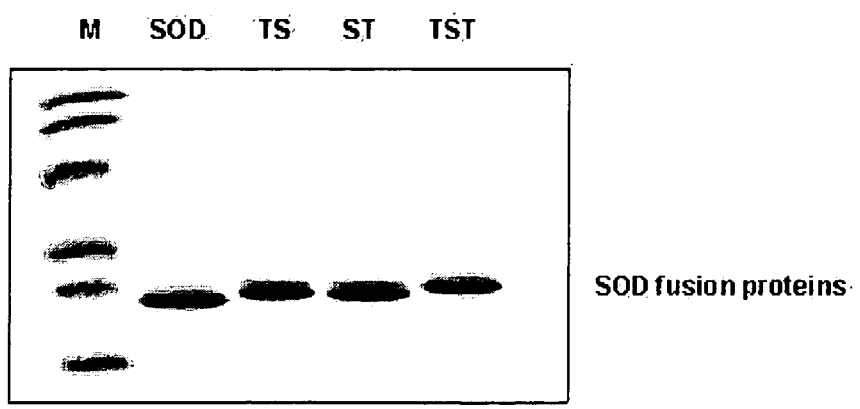

FIG. 10 shows transduction domain-GFP fusion proteins which were purified, isolated by 12% SDS-PAGE, and then stained with Coomassie blue.

Lane M: SDS marker; lane SOD: SOD; Lane TS: Tat-SOD; lane ST: SOD-Tat; and Lane TST: Tat-SOD-Tat.

FIG. 11a shows the results of Western blot analysis for intracellular transduction of Tat-SOD, SOD-Tat, Tat-SOD- Tat fusion proteins, which were purified in a denatured state, and then transduced into HeLa cells at a 2M concentration for 1 hour.

FIG. 11b is a graphic diagram showing a change in activity of an SOD enzyme, which was transduced into HeLa cells at 2M for 1 hour.

Figure 12:
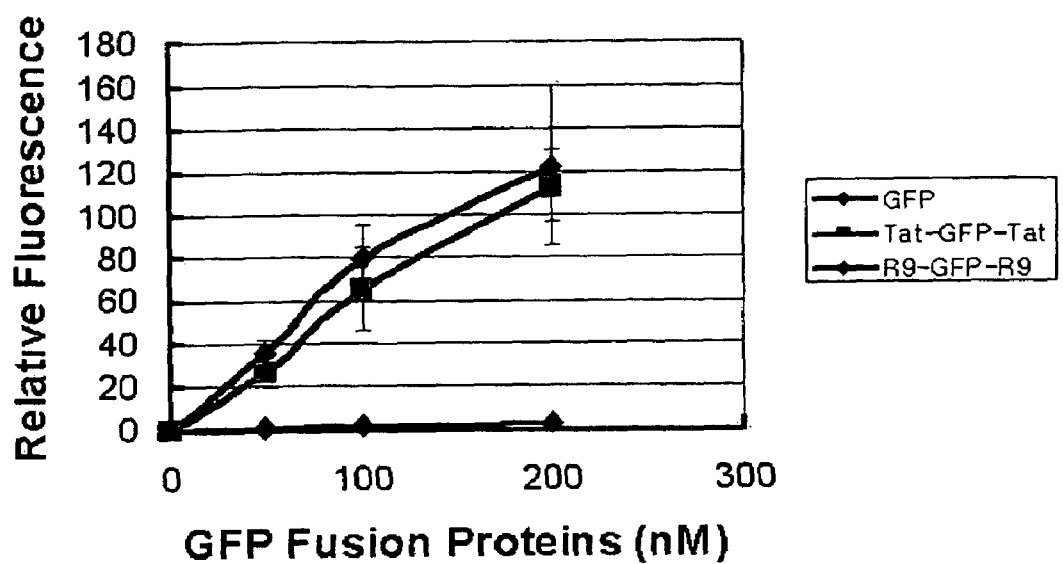

FIG. 12 is a graphic diagram showing the results of fluorescent measurement to examine the efficiency of intracellular transduction of a Tat-GFP-Tat fusion protein and an arginine 9-GFP-arginine 9 (R9-GFP-R9) fusion protein.

Figure 13:
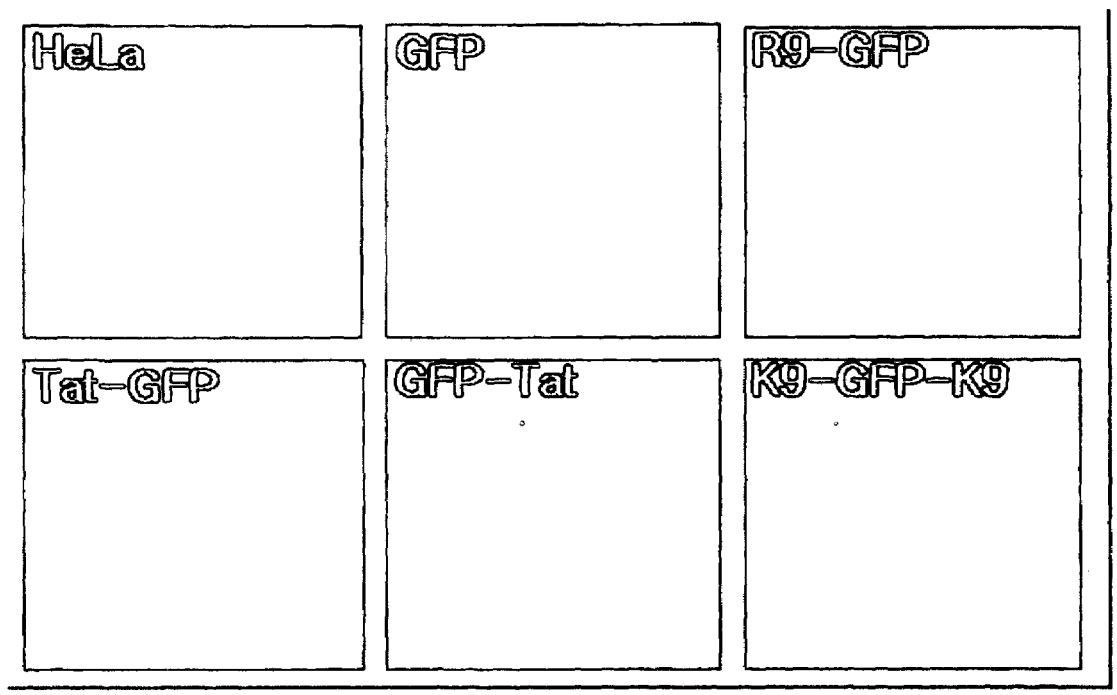

FIG. 13 is a fluorescent microscopic photograph showing the comparison between the efficiency of intracellular transduction of a GFP fusion protein, a Tat-GFP fusion protein, a GFP-Tat fusion protein, an arginine 9-GFP fusion protein, and a lysine-GFP-lysine 9 (K9-GFP-K9) fusion protein. Each of the fusion proteins was added to HeLa cells at 200 nM and then the cells were cultured for one hour.

BEST MODE FOR CARRYING OUT THE INVENTION

The present invention will hereinafter be described in further detail by examples. It will however be obvious to a person skilled in the art that that the present invention is not limited to or by the examples.

EXAMPLE 1

Production of Transduction Domain Fusion Protein Expression Vector

To develop a technology of delivering a functional protein or peptide into a cell, fusion protein expression vectors capable of delivering the target protein into the cell were produced.

Figure 1:
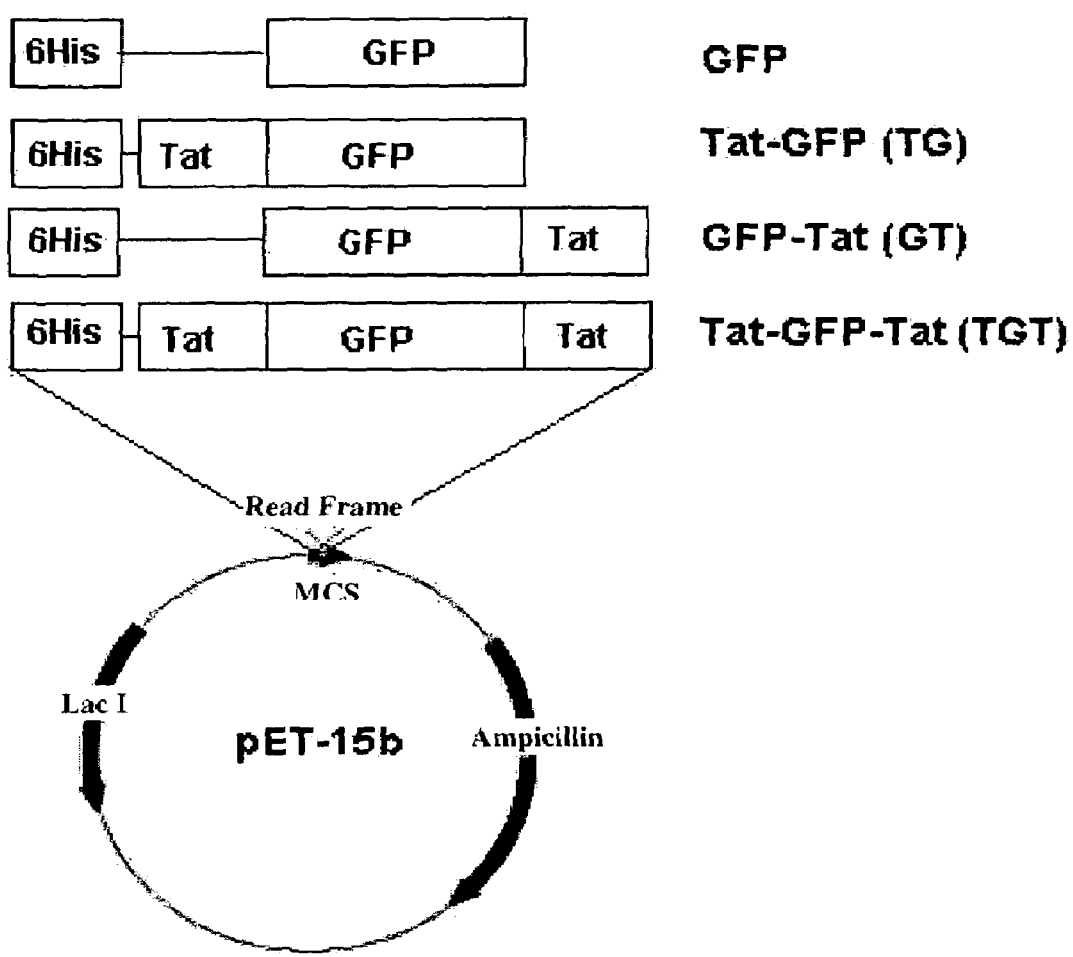
FIG. 1 is a schematic diagram of Tat-GFP, GFP-Tat, Tat-GFP-Tat, and GFP expression vectors. Such vectors were produced by fusing a synthesized Tat transduction domain to the amino-terminal end or carboxyl-terminal end or both terminal ends of GFP. GFP expression vector pGFP was produced by inserting the coding sequence of GFP into pET 15b.

In this example, to facilitate the analysis of the ability of a transduction domain to deliver a target protein into a cell, a green fluorescence protein (referred to as "GFP" in the specification) was selected as a target protein. A DNA fragment corresponding to the base sequence of GFP was subjected to polymerase chain reaction (PCR) using plasmid pEGFP-C2 (Clonetec) to amplify the complete sequence of GFP. In this PCR, the sequence of a sense primer was 5'-CTCGAGGTGAGCAAGGGCGAGGAGCTG-3' (SEQ ID NO: 1), and the sequence of an antisense primer was 5'-GGATCCTTACTTGTACAGCTCGTCC ATGCCGAG-3' (SEQ ID NO: 2). The PCR product was cut with XhoI-BamHI, and subcloned into the XhoI-BamHI site of pET15b (Invitrogen, Carlsbad, Calif.) to produce pGFP expressing a GFP fusion protein having no basic domain of HIV-1 Tat. A clone having about 0.7 kb insert was selected by XhoI-BamHI restriction enzyme analysis and sequenced.

pTat-GFP expressing the basic domain (amino acids 48-57) of HIV-1 Tat fused to GFP was produced in the following method. First, two oligonucleotides were produced and annealed into double-stranded oligonucleotides coding for 9 amino acids of the basic domain of HIV-1 Tat. The sequences coding for 9 amino acids of the basic domain of HIV-1 Tat were a top strand of 5'-TAGGAAGAAGCG-GAGACAGCGACGAAGAC-3' (SEQ ID NO: 3) and a bottom strand of 5'-TCGAGTCTTCGTCGCTGTCTC-CGCTTCTTCC-3' (SEQ ID NO: 4). The double-stranded oligonucleotides were connected directly to a site of pGFP digested with NdeI-XhoI. Thus, Tat-GFP expression plasmid pTat-GFP which had been connected with 6-histidine open reading frame in frame, was produced (FIG. 1).

Furthermore, to produce pTat-GFP-Tat where the Tat basic domain was fused to both terminal ends, a double-stranded oligonucleotide coding for 9 amino acids of the Tat basic domain was annealed into pTat-GFP and inserted into the carboxyl-terminal end. To produce pGFP-Tat where the Tat basic terminal end was fused to the carboxyl-terminal end, a double-stranded oligonucleotide coding for 9 amino acid of the Tat basic domain was annealed into pGFP and inserted into the carboxyl terminal end (FIG. 1).

The sequence of the oligonucleotide cloned into the plasmid was analyzed with a fluorescence-based automated sequencer (Model 373A, Applied Biosystems, Inc.).

EXAMPLE 2

Expression and Purification of Tat-GFP, GFP-Tat and Tat-GFP-Tat Fusion Proteins (Native and Denatured States)

*E. coli* BL21 (Pharmacia) transformed with pGFP and pTat-GFP, pGFP-Tat and pTat-GFP-Tat, and the like, was selected, and then the colony was inoculated to an LB medium containing 100 μg/ml ampicillin and cultured at 37° C. overnight. The cultured medium was 10-fold diluted in a fresh LB medium and cultured with stirring at 250 rpm. When the bacterial concentration (the optical density at a 600 nm wavelength) in the cultured medium reached 1.0, IPTG was added into the cultured medium to a final concentration of 0.5 mM and then the cells were cultured for 4 hours.

Figure 2:
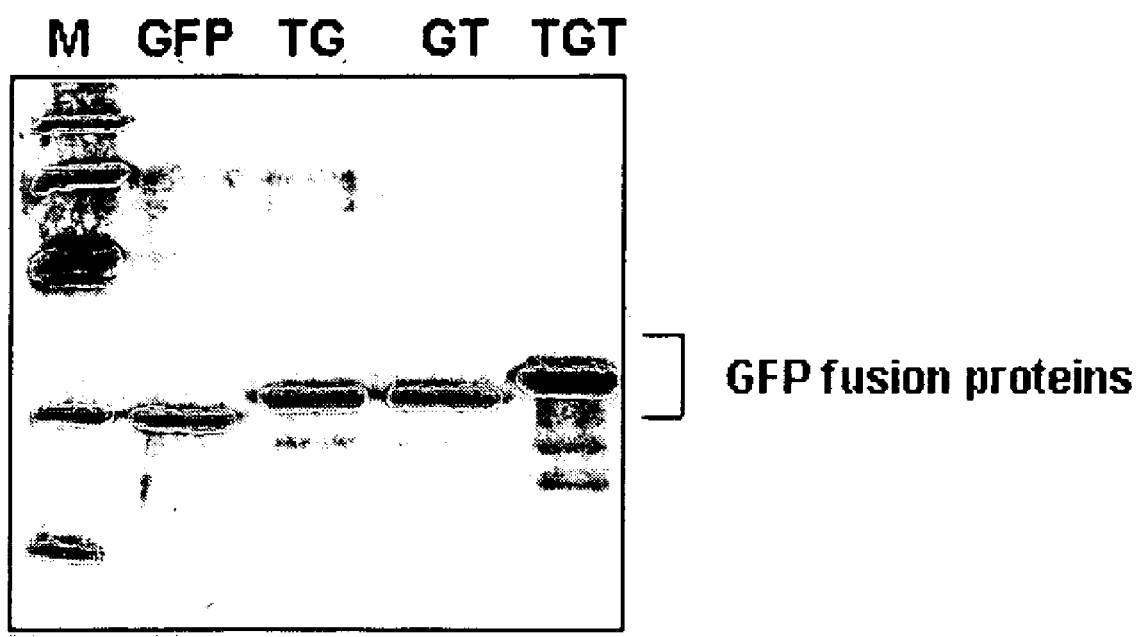
FIG. 2 shows a transduction domain-GFP fusion protein which was purified, isolated by 12% SDS-PAGE, and then stained with Coomassie blue.

To obtain the cultured cells were added to a denatured transduction domain-GFP fusion protein, a binding buffer (5 mM imidazole, 0.5M NaCl, 20 mM Tris-HCl, pH 7.9) containing 6M urea and a protease inhibitor (20 mg/ml soybean trypsin inhibitor, 2 mg/ml aprotinin, 5 mg/ml leupeptin, 100 mg/ml PMSF). The mixture was subjected to sonication, harvested and lysated. The resulting substance was placed in buffer A (6M urea, 20 mM HEPES, pH 8.0, 100 mM NaCl), subjected to sonication to disrupt the cell, and then subjected to two consecutive centrifugations (at 16,500 rpm for 30 min, and then 40,000 rpm for 30 min, each at 4° C.) to remove insoluble cell debris. The lysate was purified through a $Ni^{+++}$-IDA column. The column was washed with a binding buffer containing no 6M urea, and then with a washing buffer (80 mM imidazole, 0.5M NaCl, 20 mM Tris-HCl, pH 7.9). The protein was eluted with an elution buffer (1 mM imidazole, 0.5M NaCl, 20 mM Tris-HCl, pH 7.9), and then purified through PD-10 column chromatography (Amersham) to remove salts contained in the protein (FIG. 2). The purified GFP fusion protein was expressed and purified into about 30 kDa size, the Tat-GFP and GFP-Tat fusion proteins were expressed and purified to a size as large as the size (about 1 kDa) of the Tat transduction domain, and the Tat-GFP-Tat fusion protein had the Tat transduction domains fused to both sides thereof, and thus expressed and purified to a molecular weight greater than the Tat-GFP and GFP-Tat fusion proteins by the size of one Tat transduction domain.

A native, transduction domain-GFP fusion protein was produced by the same procedures without the above-mentioned denaturing agent. Each fraction was isolated by SDS-PAGE and then quantified using a bovine serum albumin (BSA) standard by an optical density measurement method. The protein concentration was determined by Bradford protein assay (Biorad). The purified proteins were dissolved in PBS containing 20% glycerol, and stored at −80° C.

EXAMPLE 3

Culturing of Cells and Test of Intracellular Transduction of Fusion Proteins HeLa cells were cultured in DMEM (Dulbecco's modified eagle's medium) containing 20 mM HEPES/NaOH (pH 7.4), 5 mM NaHCO3, 10% fetal bovine serum (FBS) and antibiotics (100 μg/ml streptomycin, 100 U/ml penicillin) at 37° C.

In order to observe the intracellular transduction of a transduction domain fusion protein where a HIV-1 Tat protein transduction domain consisting of 9 amino acids (49-57) was bound to the amino-terminal end and/or the carboxyl-terminal end, the following test was performed. Namely, in order to observe the ability of transduction domain-GFP, GFP-transduction domain, transduction domain-GFP-transduction domain fusion proteins to be transduced into cells, the HeLa cells were grown on a 6-well plate for 4-6 hours, and replaced by a fresh DMEM culture medium containing 10% FBS, and then GFP fusion proteins were added to the cultured medium at various concentrations. After culturing at 37 □ for 1 hour, the cells were sufficiently washed with phosphate buffered saline (PBS), and treated with trypsin-EDTA (Gibco BRL) for 10 minutes. After the cells were disrupted, the amount of the transduction domain-GFP fusion protein transduced into the cell was measured by Western blot analysis as described in the following example.

EXAMPLE 4

Western Blot Analysis

In order to analyze the efficiency of intracellular transduction of the fusion protein where one Tat transduction domain is fused to the amino-terminal end as well as the fusion protein where Tat transduction domains are fused to both terminal ends, Western blot analysis was performed as follows. First, proteins were purified in a denatured state. Prepared animal HeLa cells were treated with 1M of the denatured proteins, and after one hour, only the cells were collected and subjected to Western blot analysis. The cells were lysated, and the resulting cell lysates were placed into a 6-well plate containing an elution buffer (125 mM Tris-HCl, pH 6.8, 2% SDS, 10% v/v glycerol). Each 15 μg of the cell lysates was electrophoresed on SDS-12% polyacrylamide gel.

Figure 3:
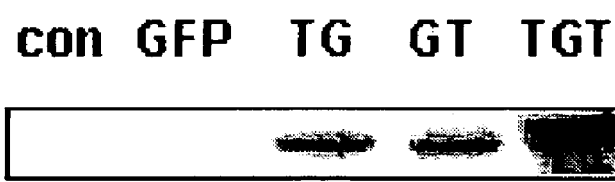
Figure 3:
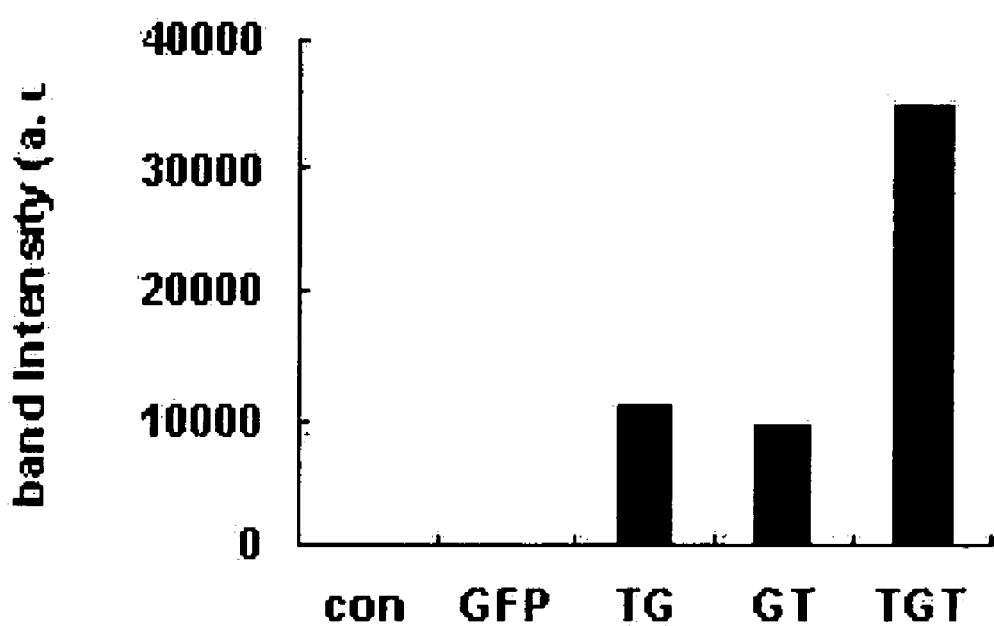

The protein separated by the electrophoresis was transferred to a nitrocellulose membrane (Amersham, UK). The nitrocellulose membrane to which the protein had been transferred was blocked with PBS containing 10% dry milk. Then, the membrane was treated with a rabbit anti-GFP polyclonal antibody (Clontech, USA, 1:1,000). Next, it was reacted with a Horseradish peroxidase-bound goat anti-rabbit IgG antibody (Sigma, 1:10,000 dilution). The bound antibodies could be detected by enhanced chemiluminescence (ECL; Amersham). As shown in FIG. 3, the results showed that the fusion protein having the Tat transduction domain only at the amino-terminal end and the fusion protein having the Tat transduction domain at the carboxyl-terminal end were transduced into the cells in similar amounts. However, the protein where the Tat transduction domains had been fused to both terminal ends was transduced into the cell in a more efficient manner than the fusion protein to which one Tat transduction domain had been fused. Such results indicate that whether the Tat transduction domain is fused to the amino-terminal end or fused to carboxyl terminal end of the fusion proteins, it shows similar effects on the intracellular delivery of the target protein, but if the Tat transduction domain is fused to both terminal ends of the fusion protein, its effect on the intracellular delivery of the target protein will be greatly improved.

EXAMPLE 5

Analysis of Intracellular Transduction by Confocal Microscopy

In transducing fusion proteins into target cells, the ratio of the cells into which the fusion proteins are transduced is important. Furthermore, only if the fusion proteins transduced into the cells maintain their inherent activity, this protein transduction technology can be applied. Thus, in this example, the ratio of cells into which the GFP fusion protein is transduced, or whether the transduced fusion protein has activity or not, was analyzed. The fluorescent intensity of GFP in HeLa cells treated with a denatured GFP fusion protein was observed with a fluorescent microscope.

The cells were cultured to 50-70% confluency on a cover slip, and treated with 1M of a GFP-fusion protein having transduction domains bound to both terminal ends thereof, and then cultured for 15 minutes. The HeLa cells were washed two times with PBS, and treated with trypsin, and then immobilized with PBS containing formaldehyde at room temperature for 15 minutes. The cells were washed with PBS again and treated with 2 g/ml of propidium iodide (PI) for 15 minutes to stain only nuclei. The cells were washed with PBS again, and treated with a mounting solution (phosphate buffered saline (PBS) containing 90% glycerol and 0.1% phenylenediamine), and covered with a cover glass. Then, whether the cells have fluorescence or not was observed with 488 nm and 545 nm fluorescent filters using a confocal fluorescent microscope to analyze the distribution of the proteins in the cells (Eric et al., 1997). The results showed that the protein having the Tat transduction domain fused to the amino-terminal end, and the protein having the Tat transduction domain fused to the carboxyl-terminal end, reached both cytoplasms and nuclei in substantially similar manners. Similarly to the results of the Western blot analysis, this suggests that whether the Tat transduction domain is fused to the amino-terminal end or fused to the carboxyl-terminal end of the proteins, it shows similar effects on the intracellular delivery of the target protein. On the other hand, the fusion protein having the Tat transduction domains fused to both terminal ends thereof showed a higher fluorescence intensity than the proteins having the Tat transduction domain only at one terminal end. In addition, the fusion protein having the Tat transduction domains fused to both terminal ends was transduced into nuclei at larger amounts.

EXAMPLE 6

Analysis of Transduction into Cells by FACS (Flow Cytometry) Analysis

In order to observe the intracellular transduction of a transduction domain fusion protein where HIV-1 Tat protein transduction domains each consisting of 9 amino acids (49-57) were bound to the amino terminal end and carboxyl terminal ends, the following test was performed (FIG. 5). Namely, in order to observe the ability for the transduction domain-GFP-transduction domain fusion protein to be transduced into cells, HeLa cells were grown on a 6-well plate for 4-6 hours, and replaced by a fresh DMEM medium containing 10% FBS, and then GFP fusion proteins were added to the cultured medium at various concentrations. After culturing at 37° C. for 30 minutes, the cells were sufficiently washed with phosphate buffered saline (PBS), and treated with trypsin-EDTA (Gibco BRL) for 10 minutes. The cells were collected, washed twice with PBS again, and immobilized with 4% paraformaldehyde for 1 hour. The intracellular fluorescence of the immobilized cells was analyzed by FACS analysis. According to the results of the FACS analysis, curves as shown in FIG. 5 were obtained. Similarly to the results as described above, it could be found that the proteins having the Tat transduction domain fused to one terminal end thereof were introduced into the cells at similar amounts whereas the fusion protein having the Tat transduction domains fused to both terminal ends thereof was introduced into increased amounts. Mean fluorescence intensity was 23.86 for the transduction domain-GFP fusion protein, 17.21 for the GFP-transduction domain fusion protein, and 204.52 for the transduction domain-GFP-transduction domain fusion protein, indicating that the transduction domain-GFP-transduction domain shows significantly increased fluorescence intensity. Then, in order to analyze the mechanism of intracellular transduction of the Tat-GFP-Tat fusion protein on the basis of its amount, the Tat-GFP-Tat fusion protein was added to the cells at various concentrations, and the mixture was cultured for 30 minutes and then subjected to FACS analysis (FIG. 6). As a result, it could be found that the fusion protein having the Tat transduction domains fused to both terminal ends thereof showed an increase in mean fluorescence intensity with an increase in its concentration.

EXAMPLE 7

Figure 7:
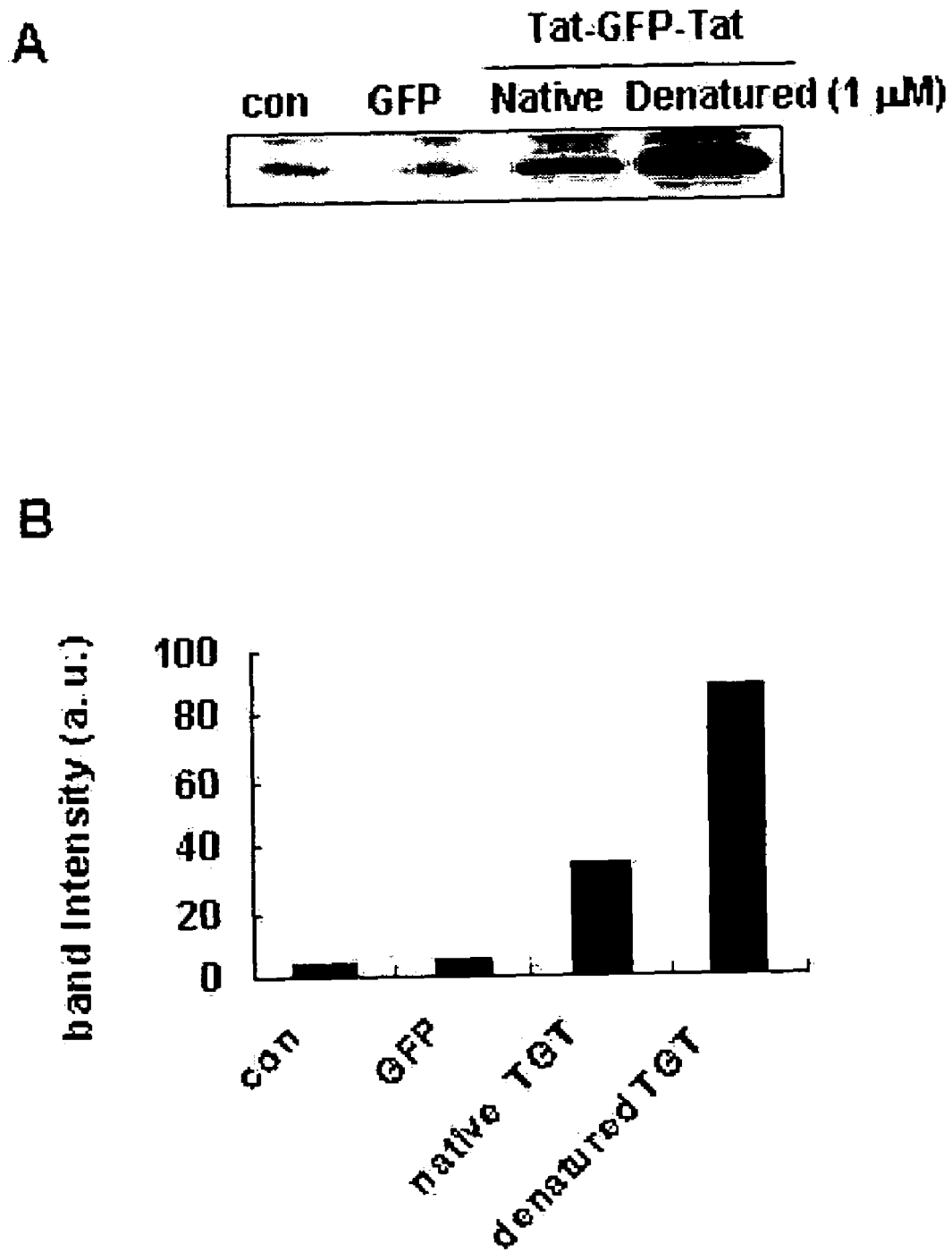

FACS (Flow Cytometry) Analysis and Western Blot Analysis for Comparison Between Intracellular Transduction of Native Fusion Protein and Denatured Fusion Protein A transduction domain-GFP fusion protein which was purified in a native state is significantly limited in intracellular transduction as compared to a transduction domain-GFP fusion protein which was purified in a denatured state. When purified in a denatured state, the GFP fusion protein having the transduction domains fused to both terminal ends thereof shows a higher effect than the GFP fusion protein having the transduction domain fused to one terminal end thereof. For this reason, in order to examine the effect of intracellular transduction of the transduction domain-GFP-transduction domain fusion protein purified in a native state, the following tests were performed. First, a protein purified in a denatured state, and a protein purified in a native state, were analyzed by Western blot analysis. The results showed that the protein purified in a native state was transduced into cells at the same level as the GFP fusion protein having one transduction domain (FIG. 7). Also, in order to examine the effect of intracellular transduction of the transduction domain-GFP-transduction domain fusion protein purified in a native state, the following test was performed. Each of the protein purified in a native state and the protein purified in a denatured state was added to cells at various concentrations and then the cells were cultured for 1 hour. As shown in FIG. 8, when the transduction domain-GFP-transduction domain fusion protein purified in a denatured state was added to cells at 1M, the mean fluorescence intensity of the cells was 117, but when the transduction domain-GFP-transduction domain fusion protein purified in a native state was added to cells, the mean fluorescence intensity of the cells was 54. This suggests that the effect of intracellular transduction of the transduction domain-GFP-transduction domain fusion protein is inferior to that of the transduction domain-GFP-transduction domain fusion protein purified in a denatured state, but equal to that of the transduction domain-GFP fusion protein purified in a denatured state as shown in FIG. 7. As a result, it can be concluded that the fusion protein, which has the Tat transduction domains at both terminal ends thereof and was purified in a denatured state, can be transduced into cells in a more effective manner than the fusion protein having the transduction domain at one terminal end, and the transduction domain-GFP-transduction domain fusion protein purified in a native state can also be transduced into cells.

EXAMPLE 8

Production of Vectors for Expression of Recombinant SOD Fusion Proteins

In order to develop a technology of delivering functional proteins or peptides into cells, fusion protein expression vectors allowing the target proteins to be delivered into cells were produced. To facilitate the analysis of the ability of the transduction domain to deliver the proteins into cells, a human Cu/Zn-superoxide dismutase (hereinafter, abbreviated to SOD) protein was selected.

To overexpress recombinant fusion proteins, Tat-SOD, SOD-Tat and Tat-SOD-Tat expression vectors each containing SOD, HIV-1 Tat transduction domain (amino acids 49-57) and cDNA for 6 histidines in order were produced (FIG. 9). To overexpress protein SOD as a control for fusion proteins, a pET-SOD expression vector containing the same domains as the above expression vectors except for the Tat transduction domain was produced.

Two oligonucleotides corresponding to a Tat basic domain and having a top strand of 5'-TAGGAAGAAGCG-GAGACAGCGACGAAGAC-3' (SEQ ID NO: 3) and a bottom strand of 5'-TCGAGTCTTCGTCGCTGTCTC-CGCTTCTTCC-3' (SEQ ID NO: 4) were cut with NdeI-XhoI restriction enzyme, and ligated into a pET-15b vector, and then two oligonucleotides were synthesized on the basis of the sequence of a human SOD cDNA. The forward primer has an XhoI restriction site, and the reverse primer has a BamHI restriction site. After performing polymerase chain reaction (PCR), the PCR product was isolated, and transformed with a TA cloning vector, thereby producing a plasmid. The human SOD cDNA transformed with the TA vector was cut with XhoI and BamHI and inserted into pET-15b and pET-15b-Tat expression vectors.

Furthermore, to produce a pTat-SOD-Tat expression vector having Tat basic domains fused to both terminal ends thereof, double stranded oligonucleotide coding for 9 amino acids of the Tat basic domain was annealed into pTat-SOD. To produce a pSOD-Tat expression vector having a Tat basic domain fused to the carboxyl terminal end, double-stranded oligonucleotide coding for 9 amino acids of the Tat basic domain was annealed into pSOD (FIG. 9).

EXAMPLE 9

Expression and Purification of Recombinant SOD Fusion Proteins

E. coli BL21 (DE3) cells (pSOD, pTat-SOD, pSOD-Tat, and pTat-SOD-Tat) which contain human Cu/Zn-superoxide dismutase cDNA and were produced by the present inventors, were placed in an LB medium containing ampicillin, and then the cells were cultured with stirring at 37° C. and 200 rpm. When the bacterial concentration (the optical density at a 600 nm wavelength) in the cultured medium reached 0.5-1.0, IPTG was added to the medium to a final concentration of 0.5 mM, and then the cells were cultured for 3-4 hours. The cultured cells were centrifuged, collected, added with 5 ml of a binding buffer (5 mM imidazole, 0.5M NaCl, 20 mM Tris-HCl, pH 7.9) containing 6M urea, and then disrupted by sonication. Immediately after centrifugation, the supernatant was loaded on a Ni-nitrilotriacetic acid Sepharose superflow column, and washed with a 10-fold volume of binding buffer and a 6-fold volume of washing buffer (60 mM imidazole, 0.5M NaCl, 20 mM Tris-HCl, pH 7.9), and then the fusion protein was eluted with elution buffer (1M imidazole, 0.5M NaCl, 20 mM Tris-HCl, pH 7.9). Next, the fractions containing the fusion protein were collected and purified by PD-10 column chromatography to remove salts contained in the fractions. Since the fusion protein contained 6 histidines, it was purified to a purity of more than 90% by metal ion-chelate affinity chromatography, single stage (FIG. 10).

The concentration of protein in the fractions was measured by a Bradford method using a fetal serum albumin standard.

EXAMPLE 10

Culturing of HeLa Cells and Intracellular Transduction of Recombinant Fusion Proteins HeLa cells were cultured in DMEM (Dulbecco's modified eagle's medium) containing 20 mM HEPES/NaOH (pH 7.4), 5 mM $NaHCO_3$, 10% fetal bovine serum (FBS) and antibiotics (100 µg/ml streptomycin, 100 U/ml penicillin) with supply of 95% air and 5% $CO_2$ at 37° C.

In order to the efficiency of intracellular transduction of transduction domain fusion proteins where a HIV-1 Tat protein transduction domain consisting of 9 amino acids (49-57) were bound to the amino-terminal end and/or the carboxyl-terminal end, the following test was performed. Namely, in order to observe the ability of Tat-SOD, SOD-Tat, and Tat-SOD-Tat fusion proteins to be transduced into cells, HeLa cells were grown on a 6-well plate for 4-6 hours, and then replaced by a fresh DMEM culture medium containing 10% FBS, and the cultured medium was treated with 2M SDS fusion proteins. After culturing the cells at 37° C. for 1 hour, the cells were sufficiently washed with phosphate buffered saline (PBS), and treated with trypsin-EDTA (Gibco BRL) for 10 minutes. After the cells were disrupted, the amount and activity of the SOD into the cells were measured by SOD activity analysis and Western blot analysis.

EXAMPLE 11

Western Blot Analysis

In order to analyze the efficiency of intracellular transduction of a protein where one Tat transduction domain is fused to the amino-terminal end as well as a protein where Tat transduction domains are fused to both terminal ends, Western blot analysis was performed as follows. First, proteins were purified in a denatured state. Prepared HeLa cells were treated with 2M of the denatured fusion proteins, and after one hour, only the cells were collected and subjected to Western blot analysis. The cells were lysated, and the resulting cell lysates were placed into a 6-well plate containing a lytic buffer (125 mM Tris-HCl, pH 6.8, 2% SDS, 10% v/v glycerol). Each 15 µg of the cell lysates was electrophoresed on SDS-12% polyacrylamide gel.

The protein separated by the electrophoresis was transferred to a nitrocellulose membrane (Amersham, UK). The nitrocellulose membrane to which the protein had been transferred was blocked with PBS containing 5% non-dry milk. Then, the membrane was treated with a goat anti-SOD polyclonal antibody (Santacruz, USA, 1:1,000). Next, it was reacted with a Horseradish peroxidase-bound mouse anti-rabbit IgG antibody (Sigma, 1:10,000 dilution). The bound antibodies could be detected by enhanced chemiluminescence (ECL; Amersham). As shown in FIG. 11a, the results showed that the fusion protein having the Tat transduction domain only at the amino-terminal end and the fusion protein having the Tat transduction domain at the carboxyl-terminal end, were transduced into the cells in similar manners. However, the protein having the Tat transduction domains fused to both terminal ends thereof was transduced into the cells in a more effective manner than the fusion protein to which one Tat transduction domain is fused. Such results indicate that whether the Tat transduction domain is fused to the amino terminal end or fused to carboxyl terminal end of the fusion protein, it shows similar effects on the intracellular delivery of the target protein, but if the Tat transduction domain is fused to both terminal ends of the fusion protein, its effect on the intracellular delivery will be greatly improved (FIG. 11a).

EXAMPLE 12

Measurement of Activity of SOD Enzyme

In this example, the activity of SOD was measured by observing the reduction of ferricytochrome c by xanthine/ xanthine oxidase with a spectrophotometer according to the method of McCord and Fridovich (McCord, J M and Fridovich, I., J. Biol. Chem. 244, 6049-6055 (1969)).

The standard analysis method was performed in 50 mM of a phosphate buffered solution (pH 7.8) containing 2 ml of 0.1 mM EDTA at 25° C. The reaction mixture contained 10 µM ferricytochrome c, 50 µM xanthine and a sufficient amount of xanthine oxidase, and the reduction of ferricytochrome c was measured at 550 nm. The amount of superoxide dismutase at which cytochrome c is reduced by 50% was defined as 1 unit.

Figure 11:
Figure 11:
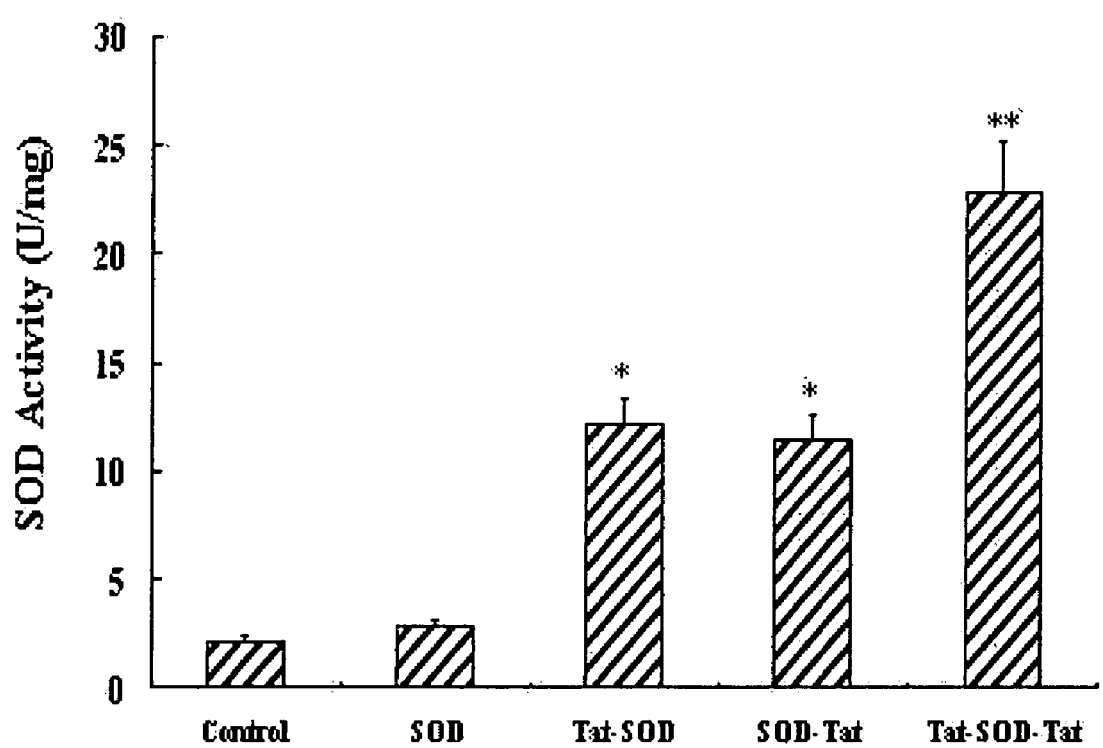

In order to make it possible to apply the fusion proteins for protein therapy, the fusion proteins transduced into cells must maintain their inherent activity. Thus, it is a very important problem that the fusion proteins transduced into cells has biological activity. FIG. 11b shows a change in enzymatic activity of SOD when 2M of fusion proteins were administered to a HeLa cell medium for 1 hour. The activity of SOD in cells to which the fusion proteins had not been administered was 2.46±0.39 U/mg protein, and the activity of SOD in cells to which the Tat-SOD and SOD-Tat fusion proteins was 12.68±1.44 U/mg protein which indicates a significant increase in the SOD activity. When the Tat-SOD-Tat fusion protein was administered to cells, the SOD activity was 23.75±2.35 U/mg protein which indicates a two times increase in the SOD activity as compared to that of the Tat-SOD and SOD-Tat fusion proteins (FIG. 11b). As a result, it could be found that the intracellular transduction and activity of the Tat-SOD-Tat fusion protein was at least two times higher than the Tat-SOD and SOD-Tat fusion proteins (FIG. 11).

EXAMPLE 13

Measurement of Ability of Arginine 9-GFP-arginine 9 Fusion Protein to be Transduced into Cells According to a similar method to Examples 1-3, an arginine-GFP-arginine fusion protein where the transduction domains each consisting of 9 arginine residues had been covalently bonded to the amino- and carboxyl-terminal ends of the green fluorescent protein (GFP) was produced.

In order to compare the efficiency of intracellular delivery of the Tat-GFP-Tat fusion protein and the arginine 9-GFP-arginine 9 (R9-GFP-R9) fusion protein, each of the fusion proteins were added to a 24-well plate containing HeLa cells, at 50 nM, 100 nM and 200 nM. After one hour, the cells were treated with trypsin, washed several times with PBS, and measured for fluorescence with a fluorometer. The results are shown in FIG. 12.

EXAMPLE 14

Measurement of Ability of Lysine 9-GFP-lysine 9 Fusion Protein to be Transduced into Cells According to a similar method to Examples 1-3, an oligolysine-GFP-oligolysine fusion protein where the transduction domains each consisting of 9 lysine residues are covalently bonded to the amino and carboxyl terminal ends of the green fluorescent protein (GFP) was produced.

In order to compare the efficiency of intracellular delivery of the Tat-GFP fusion protein, the GFP-Tat fusion protein, the arginine 9-GFP fusion protein and the lysine 9-GFP-lysine 9 (K9-GFP-K9) fusion protein, 200 nM of each of the fusion proteins was added to a 24-well plate containing HeLa cells. After one hour, the cells were treated with trypsin, washed several times with PBS, and measured for fluorescence with a fluorescent microscope. The results are shown in FIG. 13.

INDUSTRIAL APPLICABILITY

As described above, the present invention provides the fusion protein which delivers the functional proteins into cells at increased efficiency and has increased activity in the cells, as compared to the existing fusion proteins having the basic transduction domain at one terminal end.

Furthermore, the present invention provides pharmaceutical composition and cosmetics, etc., which contain the inventive fusion protein as an active ingredient.

Moreover, the present invention proposes that the transduction domain-SOD-transduction domain, which delivers the human Cu/Zn-superoxide dismutase directly into cells at a protein level, can be efficiently applied to protein therapy, since it shows increased SOD activity when delivered into the cells.

The reactive oxygen species cause damage to biopolymers, and as reported, they have a deep connection with about 10 kinds of diseases. Thus, according to the present invention, the transduction domain-SOD-transduction domain fusion protein of the present invention can be effectively used in protein therapy where the SOD playing a main role in removing such reactive oxygen species is delivered into cells to treat diseases.

According to the present invention, the SOD that is a kind of antioxidant enzymes can be delivered into cells to remove the reactive oxygen species harmful to the human body. Thus, the present invention can be used in a wide range of industrial fields, including the cosmetic and health food industries, in addition to treating various diseases.

---

What is claimed is:

1. A transduction domain-target protein-transduction domain fusion protein having the ability to be transduced into a cell, wherein the target protein is a Cu/Zn-superoxide dismutase and the transduction domains comprise HIV tat residues 49-57 and are covalently bonded to each of the amino- and carboxyl-terminal ends of the target protein.

2. A cosmetic composition comprising the transduction domain-target protein-transduction domain fusion protein of claim 1 as an active ingredient.

3. The cosmetic composition of claim 2, which is in the form of toilet water, gel, water-soluble liquid, oil-in-water (O/W), or water-in-oil (W/O).

4. A pharmaceutical composition comprising: the transduction domain-target protein-transduction domain fusion protein of claim 1 as an active ingredient, and a pharmaceutically acceptable carrier.

* * * * *

UNITED STATES PATENT AND TRADEMARK OFFICE
CERTIFICATE OF CORRECTION

PATENT NO. : 7,306,944 B2  Page 1 of 1
APPLICATION NO. : 10/488743
DATED : December 11, 2007
INVENTOR(S) : Su-Young Choi et al.

It is certified that error appears in the above-identified patent and that said Letters Patent is hereby corrected as shown below:

On Title page
Items (75) Inventor: replace the name "Jin-Hee Choi" with the name -- Jin-Hi Choi --.

Signed and Sealed this

Thirteenth Day of May, 2008

JON W. DUDAS
*Director of the United States Patent and Trademark Office*

UNITED STATES PATENT AND TRADEMARK OFFICE
CERTIFICATE OF CORRECTION

PATENT NO. : 7,306,944 B2  Page 1 of 1
APPLICATION NO. : 10/488743
DATED : December 11, 2007
INVENTOR(S) : Soo Young Choi et al.

It is certified that error appears in the above-identified patent and that said Letters Patent is hereby corrected as shown below:

On Title page
Items (75) Inventors:
"Su-Young Choi" with the name -- Soo Young Choi --
"Jin-Seo Park" with the name -- Jinseu Park --
"Kyu-Hyung Han" with the name -- Kyuhyung Han --

Signed and Sealed this

Second Day of March, 2010

David J. Kappos
*Director of the United States Patent and Trademark Office*